(12) United States Patent
Harvey et al.

(10) Patent No.: US 7,022,350 B2
(45) Date of Patent: Apr. 4, 2006

(54) DIETARY SUPPLEMENT

(75) Inventors: Bryce M. Harvey, Pike Road, AL (US); Philip M. Knight, Pike Road, AL (US)

(73) Assignee: Proethic Pharmaceuticals, Inc., Montgomery, AL (US)

( * ) Notice: Subject to any disclaimer, the term of this patent is extended or adjusted under 35 U.S.C. 154(b) by 0 days.

(21) Appl. No.: 10/832,950

(22) Filed: Apr. 27, 2004

(65) Prior Publication Data

US 2005/0191368 A1    Sep. 1, 2005

Related U.S. Application Data

(63) Continuation-in-part of application No. 10/787,350, filed on Feb. 26, 2004, now abandoned.

(51) Int. Cl.
*A61K 35/78* (2006.01)

(52) U.S. Cl. .............. 424/727; 424/737; 424/758; 424/458; 424/641; 424/702; 514/458

(58) Field of Classification Search ......... 424/727, 424/737, 758, 458, 641, 702; 514/458
See application file for complete search history.

(56) References Cited

U.S. PATENT DOCUMENTS

| | | |
|---|---|---|
| 5,543,146 A | 8/1996 | Perez |
| 5,654,333 A * | 8/1997 | Samid ................ 514/538 |
| 6,197,309 B1 | 3/2001 | Wheeler |
| 6,361,800 B1 | 3/2002 | Cooper et al. |
| 6,482,447 B1 | 11/2002 | Revel |
| 6,511,675 B1 | 1/2003 | Siddiqui et al. |
| 2002/0156023 A1 * | 10/2002 | Walling et al. ........... 514/27 |
| 2002/0172721 A1 | 11/2002 | Boulos et al. |
| 2004/0005311 A1 | 1/2004 | Pitman |

OTHER PUBLICATIONS

Fleshner (Urol Clin N Am (2002), vol., 29, pp. 107-113).*

* cited by examiner

*Primary Examiner*—Susan D. Coe
(74) *Attorney, Agent, or Firm*—C. Brandon Browning; Sirote & Permutt P.C.

(57) ABSTRACT

A dietary supplement for treating or preventing prostate disease and/or vascular disease including saw palmetto, d-alpha tocopherol, d-gamma tocopherol, d-delta tocopherol, d-beta tocopherol, selenium, lycopene, zinc, folic acid, vitamin $B_{12}$, and vitamin $B_6$, each in a therapeutically effective amount.

30 Claims, No Drawings

DIETARY SUPPLEMENT

The present application is a continuation in part of U.S. Ser. No. 10/787,350, filed Feb. 26, 2004 now abandoned.

FIELD OF INVENTION

The present invention relates generally to a dietary supplement including vitamins, micronutrients and phytotherapeutic compounds, the supplement being adapted for administration to a host for treating or preventing conditions related to aging. More particularly, this invention relates to a dietary supplement adapted for administration to a male host for treating or preventing prostate disease and/or vascular disease, the active components of the supplement including saw palmetto, vitamin E, selenium, lycopene, zinc, vitamin $B_{12}$, vitamin $B_6$ and folic acid.

BACKGROUND OF THE INVENTION

Aging often leads to abnormally high or abnormally low concentrations of certain enzymes, hormones, vitamins, minerals or other natural elements, thereby affecting metabolism and ultimately causing disease in a host. Frequently, these diseases can be treated or prevented by simply supplementing the missing natural elements. Such diseases include, for example, cardiovascular disease, cancer and cerebrovascular disease (stroke), diseases which together represent the three most common causes of death in men over the age of 65 in the United States.

A major cause of cardiovascular disease and cerebrovascular disease is elevated serum levels of the metabolite homocysteine. Elevated homocysteine levels have been shown to be an independent risk factor for heart disease and stroke, and high levels of circulating homocysteine are believed to damage coronary arteries or make it easier for platelets to clump together and form a clot. Studies have shown that high serum homocysteine-related blood vessel damage may account for up to 20% of heart attacks, 40% of strokes and 60% of peripheral venous occlusions in the United States.

It is known that intracellular deficiencies of vitamins $B_{12}$, folic acid and $B_6$, alone or in combination, occur commonly in the elderly population and that there is a high prevalence of homocysteinemia as a syndrome of vitamin shortage in elderly subjects. Inadequate plasma concentrations of one or more of vitamins $B_{12}$, folic acid and $B_6$ are thought to contribute up to 67% of the cases of high homocysteine in the elderly. Thus, oral vitamin formulations combining vitamin $B_{12}$ (cobalamin, cyanocobalamin) folic acid (folate, folacin) and vitamin $B_6$ (pyridoxine, pyridoxal, pyridoxamine) have been used successfully in the treatment of elevated serum levels of homocysteine, as well as in lowering serum metabolite levels of homocysteine in at risk populations, such as the elderly, where homocysteine levels are not elevated but the patients are at risk for or have neuropsychiatric, vascular, renal, or hematologic diseases.

Another age-related disease that can be treated or prevented by supplementing missing natural elements is benign prostatic hypertrophy (BHP). BHP afflicts more than half of the men in the United States between the ages of 60 and 70 and as many as 90 percent between the ages of 70 and 90.

BHP is a benign condition that occurs when the male body begins to transform testosterone into dihydroxytestosterone (DHT) within the prostrate. This is primarily due to higher levels of the enzyme reductase which causes the conversion of testosterone to DHT which binds to prostatic receptor cells ultimately resulting in prostate enlargement. As the prostate grows larger it presses against the urethra and bladder, interfering with the normal flow of urine. Enlargement of the prostate gland can cause many uncomfortable symptoms including a need to urinate often, a weak or interrupted urinary stream, a feeling that you cannot empty your bladder completely, a feeling of delay or hesitation when you start to urinate, a feeling that you must urinate right away and continuing pain in the lower back, pelvis or upper thighs. Because these symptoms can cause great discomfort, BHP is typically detected early on, and men suffering from of BHP often seek treatment of the disease.

In some cases the transformation of testosterone to DHT is believed to cause prostate cancer. In the United States, prostate cancer is the most common male cancer and the second leading cause of cancer deaths in men. Prostate cancer has an incidence of approximately one case in every 10 men. Almost half of all men under 70 years old have at least microscopic prostate tumors. By age 80 to 90, seventy to ninety percent of men also portray such signs. Unlike BHP, early detection and treatment of prostate cancer is hindered since prostate cancer lacks symptoms in men with localized tumors.

The use of plants and herbs for treating prostate disease has been growing steadily in most countries. In the United States their use has also markedly increased. They are readily available as nonprescription dietary supplements and are often recommended in natural health food stores or books for self treatment of BPH symptoms. A recent survey demonstrated that one third of men choosing nonsurgical therapy for BHP utilize herbal preparations alone or in combination with prescription medications. There are about 30 phytotherapeutic compounds available for the treatment of BPH including, for example, saw palmetto, stinging nettle, pumpkin seed, *Pygeum africanum* (*Pygeum*) and *Echinacea*.

The most widely used of the plant pharmaceuticals is the extract of the American saw palmetto or dwarf palm plant, *Serenoa repens*. Saw palmetto contains fatty acids (lauric, myristic, oleic, linoleic and linolenic), phytosterols (beta-sitosterol and its glucosides, stigmasterol and campesterol) and high molecular weight fatty alcohols (docosanol, hexacosanol, octacosanol and triacontanol). While the exact mechanism by which saw palmetto works is unknown, proposed mechanisms of action include alteration in cholesterol metabolism, antiestrogenic and antiadrogenic effects, anti-inflammatory effects and a decrease in available sex horomone-binding globulin (SHB). SHBG is a plasma glycoprotein that binds to circulating plasma steroids (i.e., testosterone, DHT and estradiol), thus regulating plasma levels of free steroids. Saw palmetto is also associated with prostatic epithelial contraction, improved urinary flow, reduced residual bladder urine volume, increased ease in commencing urination, decreased frequency of urination and decreased need to empty the bladder at night.

Stinging nettle (*Urtica dioica*) has been used in the herbal treatment of BPH and prostate cancer. Stinging nettle produces a lectin that to binds to SHBG thereby preventing SHBG from binding to its receptors on various sex glands, including the prostate and testes. In the absence of the SHBG ligand, hormone up-take is prevented by glandular cells thereby effectively reducing plasma levels of testosterone.

*Pygeum* works as an anti-inflammatory agent and improves urinary symptoms. *Pygeum* contains three groups of active lipid-soluble substances: phystosterols, pentacyclic triterpenoids and ferulic esters of fatty acid alcohols. Phytosterols, particularly, beta-isoterols have been shown to reduce elevated levels of prostaglandins in those suffering from BPH. The triterpenoids are effective anti-edema agents, and the ferulic esters of fatty acid alcohols help to inhibit the absorption and metabolism of cholesterol.

Pumpkin seeds exhibit an anti-prostatic effect resulting from the sterols and fatty acids, such as palmitic, stearic, oleic and linoleic acids, contained in the oil fraction of the seeds. The oil fraction of pumpkin seed has also been shown to inhibit 5 alpha-reductase and the binding of DHT to androgen receptors. Tocopherol present in pumpkin seed oil may also regulate the tone of bladder smooth muscle.

In addition to herbs and plants, vitamins and micronutrient, alone and in combination with herbs and plants, have been shown to be a beneficial means for minimizing suffering related to BHP and prostate cancer patients. For example, studies suggest that vitamin E can inhibit the growth of certain human cancer cell lines, including prostate. Vitamin E has also been shown to have an inhibitory effect on the growth of normal smooth muscle cells. Epidemiological and clinical studies have provided some evidence of an inverse relationship between vitamin E and overall cancer morbidity and mortality.

Vitamin E functions as the major lipid soluble antioxidant in cell membranes; it is a chain-breaking, free radical scavenger and inhibits lipid peroxidation specifically, biological activity relevant to carcinogen-induced DNA. It is an immune stimulant that lowers cholesterol, raises good cholesterol (i.e., HDL), protects the nervous system and protects against cardiovascular disease.

Vitamin E is actually a general name for a family of compounds called "tocopherols" and "tocotrienols." There are four tocopherols: alpha, beta, gamma, and delta. The most active form of vitamin E is alpha-tocopherol. Alpha-tocopheryl succinate has been shown to inhibit the proliferation of human prostatic tumor cells with defective cell cycle-differentiation pathways and dl-alpha tocopherol to induce apoptosis in prostate cells. Alpha tocopherol protects against free radical damage, which has been implicated in aging and cancer initiation.

Recent research suggests that vitamin E, in combination with selenium, prevents prostate cancer. Selenium is a natural vascular stimulant and immunity booster. Selenium has often been included in studies of the relationships of antioxidant micronutrients with cancer, primarily because it is a component of glutathione peroxidase, which has antioxidant activity. Selenium is an essential constituent of at least four extracellular and cellular glutathione peroxidases, three thyroidal and extrathyroidal iodothyronine 5 deiodinases, thioredoxin reductase and other selenoproteins. Selenium inhibits tumorigenesis in a variety of experimental models, and selenium inhibits the growth of human prostate carcinoma cells in vitro. Oral selenium is selectively taken up by the prostate in humans. Studies show that when the element selenium is administered to men they have 44–66% fewer prostate cancers versus those that do not get selenium. Studies further show a stronger protective association with selenium in the presence of high gamma tocopherol concentrations.

Lycopene is the red-pigmented carotenoid that gives tomatoes their color. It includes a long chain of conjugated double bonds that give lycopene its ability to neutralize free radicals. Lycopene has been shown to inhibit proliferation in various cancer cell lines, and epidemiological studies have shown an inverse association between dietary intake of lycopene and prostate cancer risk. The mechanism by which lycopene reduces prostate cancer risk is unclear; however, possible mechanisms include inhibition of growth and induction of differentiation in prostate cancer cells.

Zinc is known to prevent of prostate cancer and improve the prostatic immune system. Zinc has also been shown to have an inverse relationship with 5 alpha-reductase activity in human prostatic tissue. Vitamin $B_6$, along with zinc has been associated with a reduced risk of prostatic cancer.

OBJECTS AND SUMMARY OF THE INVENTION

A primary object of the invention is to provide a dietary supplement and method of using same for treating or preventing prostate disease and symptoms thereof.

A further primary object of the invention is to provide a dietary supplement and method of using same for treating or preventing vascular disease.

A further primary object of the invention is to provide a dietary supplement and method of using same for reducing serum levels of homocysteine.

A further primary object of the invention is to provide a dietary supplement and method of using same for treating or preventing diseases caused by elevated levels of homocysteine such as cardiovascular disease, cerebrovascular disease and peripheral vascular disease.

A further primary object of the invention is to provide a dietary supplement and method of using same for treating or preventing prostate disease and vascular disease.

A further primary object of the invention is to provide a dietary supplement and method using same for treating or preventing vitamin and micronutrient deficiencies that can result from aging.

Another primary object of the invention is to provide a dietary supplement and method of using same for treating or preventing vitamin and micronutrient deficiencies that can lead to prostate disease and/or vascular disease.

An object of the invention is to provide a method of treating or preventing vascular disease in a male host who is at risk for or suffering from vascular disease but is unaware of the risk or that he has vascular disease.

A further object of the invention is to provide a method of treating or preventing prostate disease in a male host who is at risk for or suffering from prostate disease but is unaware of the risk or that he has prostate disease.

A further object of the invention is to provide a dietary supplement and method of using same for lowering serum levels of cholesterol.

A further object of the invention is to provide a dietary supplement and method of using same for increasing serum levels of HDL.

Another object of the invention is to provide a dietary supplement and method of using same for treating or preventing cancer.

The objects of the invention are accomplished by providing a single formulation including a combination of ingredients, each of the ingredients having prostate and/or vascular health promoting properties. The ingredients can include a therapeutically effective amount of at least one of herb known to promote prostate and/or vascular health, a therapeutically effective amount of vitamin E, a therapeutically effective amount of selenium, a therapeutically effective amount of lycopene, a therapeutically effective amount of zinc, a therapeutically effective amount of folic acid, a therapeutically effective amount of vitamin $B_{12}$ and a therapeutically effective amount of vitamin $B_6$. The term "herb" as used herein refers to the whole herb or tuber, or to the seeds, leaves, stems, flowers, roots, berries or bark, or to any extract or product derived therefrom.

The methods and compositions of the present invention address the need in the art for a more effective and convenient prostate disease and/or vascular disease treatment, as set forth above. Thus, the present invention overcomes at least some of the disadvantages of the prior art therapies and methods or at least provides a useful alternative. A person skilled in the art will understand that the therapeutic effects of the compositions result from the vitamin components, the micronutrient components and the herb components, which when combined as specifically described herein act synergistically to enhance efficacy. It is this synergism between the herb component, the various vitamin components and micronutrient components that renders the administration of the dietary supplement of the present invention beneficial. As a holistic approach to promoting prostate health and vascular health, the various active ingredients were selected which possess the following biological activities: (1) anti-tumor activity; (2) immune stimulating activity; (3) anti-androgen activity; (4) anti-BPH activity; (5) activities to restore micturitional disorders; (6) anti-vascular disease activity; (7) homocysteine-reducing activity; (8) cholesterol-reducing activity; (9) HDL-increasing activity; (10) anti-thrombosis activity and (11) anti-atherosclerosis activity.

One aspect of the invention provides a composition for treating or preventing prostate disease and/or vascular disease including d-alpha tocopherol, d-gamma tocopherol, d-delta tocopherol, d-beta tocopherol, selenium, lycopene, zinc, folic acid, vitamin $B_{12}$, and vitamin $B_6$, each in a therapeutically effective amount. The various vitamins and micronutrients described herein can refer to all biologically active forms of the identified vitamin or micronutrient, whether derived from natural or synthetic sources. For example, zinc can include zinc gluconate, zinc acetate or zinc oxide, alpha tocopherol can include alpha tocopheryl succinate or alpha tocopheryl acetate, vitamin $B_{12}$ can include cobalamin or cyanocobalamin, and vitamin $B_6$ can include pyridoxine, pyridoxal, pyridoxamine or pyridoxine HCL.

According to further aspect of the invention, a composition for treating or preventing prostate disease and/or vascular disease includes the following ingredients, each in a therapeutically effective amount: a first component selected from the group consisting of *Echinacea*, saw palmetto, stinging nettle, pumpkin seed, *Pygeum* and combinations thereof, a vitamin E component, a zinc component, a vitamin B component, and optionally a selenium component and/or a lycopene component.

According to a further aspect of the invention, a composition for treating or preventing prostate disease and/or vascular disease includes the following ingredients, each in a therapeutically effective amount: saw palmetto, d-alpha tocopherol, d-gamma tocopherol, d-delta tocopherol, d-beta tocopherol, selenium, lycopene, zinc, folic acid, vitamin $B_{12}$, and vitamin $B_6$.

According to another aspect of the invention, a method of treating or preventing prostate disease and/or vascular disease includes periodically administering orally a single formulation including a therapeutically effective amount of a first component selected from the group consisting of *Echinacea*, saw palmetto, stinging nettle, pumpkin seed, *Pygeum* and combinations thereof, a therapeutically effective amount of a vitamin E component, a therapeutically effective amount of a vitamin B component, a therapeutically effective amount of a selenium component and a therapeutically effective amount of a lycopene component.

According to an additional aspect of the invention, the compositions of the present invention are essentially free of compounds that if included in the compositions would tend to reduce the effectiveness of the compositions with regard to treating or preventing prostate disease or vascular disease. For example, according to this aspect, vitamin D is excluded from the compositions since vitamin D administration is known to result in hypercalcemia and hyperphosphatemia, which can cause atherosclerosis, accelerate vascular disease and hasten death. Similarly, vitamin C, thiamine, iron and copper are excluded since they are known to decrease vitamin $B_{12}$ levels, while vitamin A derived from animal sources is excluded since it is known that animal-derived vitamin A can increase the risk of prostate cancer. One skilled in the art will understand that there are compounds in addition to those described above that can be excluded from the present compositions for preventing a reduction in the efficacy of the composition.

The beneficial effects of the present invention include the promotion and maintenance of prostate health and vascular health. With regard to prostate health, this can include the elimination or improvement of lower urinary tract symptoms by reducing prostate inflammation and urethra compression by swelling of the prostate, the prevention of the need for prostate surgery, the prevention of prostate cancer, the improvement of a patient's stream size and strength and the elimination or improvement of symptoms of prostatitis. With regard to vascular health, this can include the lowering of serum metabolite levels of homocysteine, methylmalonic acid, cystathionine or 2-methylcitric acid, the lowering of cholesterol levels, the raising of HDL levels and the regulation of the proliferation of the cells lining the arterial walls.

Another beneficial effect of the present invention is its ability to promote both prostate and vascular health. More particularly, many men unknowingly suffer from cardiovascular disease, peripheral vascular disease or cerebrovascular disease, and often these men do not receive treatment since the symptoms of these diseases are not easily recognized. Thus, by the time these men finally suffer recognizable symptoms of vascular disease, such as heart attack or stroke, or are diagnosed, the severity of the vascular disease may have become life-threatening. The same can be said of prostate cancer, which is characterized by minute, localized tumours in the prostate that often go unnoticed.

The present invention addresses this dilemma by providing means of treating and preventing two broad classes of diseases, prostate disease and vascular disease, diseases that are prevalent among men but that have aspects which can go unnoticed and consequently untreated. By providing the dietary supplement of the present invention, one which has little or no side effects and is capable of addressing the causes and symptoms of both vascular disease and prostate disease, men are now able to receive a treatment or a preventative for a disease or diseases from which they unknowingly suffer or at risk from suffering.

The effectiveness of the present invention is due in part to the prevalence of both prostate and vascular diseases in men, the prevalence of prostate and vascular diseases in older men, the pronounced symptoms of BHP, which typically prompt men to seek treatment, and the early onset of symptoms of vascular disease such as stroke or heart attack. Thus, for example, by administering the composition of the present invention to a man who has suffered a mild heart attack or stroke at a relatively young age, possibly caused by elevated homocysteine levels, prostate disease, including prostate cancer and BHP, can be prevented and possibly unknowingly treated.

It will be apparent to those skilled in the art that only the preferred embodiments have been described by way of exemplification and that there are various modifications which fall within the scope of this invention. These and other aspects of the invention will be discussed in greater detail below.

DETAILED DESCRIPTION

The composition of this invention includes a combination of herbs, vitamins, phytochemicals and micronutrients that were specifically chosen and combined according to their biological activities. Thus, the composition includes an herbal component selected from the group consisting of *Echinacea*, saw palmetto, stinging nettle, pumpkin seed, *Pygeum* and combinations thereof, a vitamin E component including d-alpha tocopherol, d-gamma tocopherol, d-beta tocopherol and d-delta tocopherol, a vitamin B component including folic acid, vitamin $B_{12}$ and vitamin $B_6$, selenium, lycopene and zinc.

Each herb component is well characterized and has been used individually for the treatment of BPH or the prevention of prostate cancer. Some of the herb components are also known to prevent vascular disease. Unless otherwise indicated, each percentage referred to herein refers to the percentage of the active ingredients or components in the composition only and not the percentage of the whole composition.

Saw palmetto reduces prostatic inflammation and swelling and improves uncomfortable urinary symptoms. Saw palmetto inhibits 50% of the binding of DHT to receptor sites in the prostate thereby blocking the uptake of DHT into the nucleus of prostate cells. Saw palmetto also inhibits the action of testosterone 5 alpha-reductase thereby reducing the conversion of testosterone to DHT. The fatty acids, notably lauric and myristic acids, present in saw palmetto extract are mainly responsible for 5 alpha-reductase inhibition. Saw palmetto improves urinary flow, reduces residual bladder urine volume, increases ease in commencing urination, decreases frequency of urination and decreases the need to empty the bladder at night. When used in the composition, saw palmetto is present in an amount ranging from about 45% to 86% by weight, preferably 60% to 80% by weight, and most preferably about 76% by weight and contains about 45% fatty acids and sterols.

*Pygeum* is used in the treatment of BHP. *Pygeum* works as an anti-inflammatory agent and improves urinary symptoms. It is a source of phytosterol. When used in the composition, it is present in an amount ranging from about 4% to 15% by weight, preferably 7% to 12% by weight, and most preferably about 9% by weight and contains about 2.0% to 2.5% steroids.

Stinging nettle, an antioxidant and a source of Vitamin E and phytosterol, is used in the treatment of BPH and prostate cancer and has diuretic properties. Stinging nettle is also used in the treatment and prevention of vascular disease. When used in the composition, stinging nettle is present in an amount ranging from about 1% to 20% by weight, preferably 4% to 15% by weight, and most preferably about 7% by weight and contains 0.8% sterols.

Pumpkin seed, an antioxidant, contains essential fatty acids and is a source of zinc and phytosterols. Pumpkin seed is an anti-inflammatory and is used in the treatment of impotency and swollen prostate. When used in the composition, pumpkin seed is present in an amount ranging from about 5% to 30% by weight, preferably 10% to 25% by weight, and most preferably about 18% by weight.

*Echinacea* simulates immune response. It contains several potent antioxidant compounds, such as echinacoside and caffeoyl derivative. When used in the composition, *Echinacea* is present in an amount ranging from about 0.2% to 5% by weight, preferably 1% to 4% by weight, and most preferably about 2% by weight.

Vitamin E is an antioxidant known to reduce prostate cancer and an immune stimulant that lower cholesterol, raises HDL, protects the nervous system and protects against cardiovascular disease. The vitamin regulates the way that cells lining the arteries proliferate and repair themselves thereby preventing the formation of blockages on the artery walls. There is an inverse association between plasma vitamin E levels and the incidence of heart disease. Vitamin E has been shown to work in synergy with selenium.

Physiological concentrations of alpha tocopherol are known to inhibit aorta smooth muscle cell (VSMC, line A7r5) proliferation and protein kinase C (PKC) activity. Alpha tocopherol inhibition of PKC and of VSMC proliferation may represent a physiological mechanism, relevant to the onset of diseased states such as atherosclerosis. Gamma tocopherol demonstrates a greater inhibitory activity and at far lower concentrations than synthetic alpha tocopherol and has been found to be superior to alpha tocopherol in terms of cell inhibition in vitro.

When used in the composition, vitamin E is present as d-alpha tocopherol in an amount ranging from about 10% to 35% by weight, preferably 12% to 20% by weight, and most preferably about 15% by weight; d-gamma tocopherol in an amount ranging from about 1% to about 9% by weight, preferably 2% to 7% by weight, and most preferably about 3% by weight, and mixed tocopherols including d-beta tocopherol and d-delta tocopherol in an amount ranging from about 0.5% to about 6% by weight, preferably 0.75% to 3% by weight, and most preferably about 1% by weight. When the composition does not include an herb component, vitamin E is present as d-alpha tocopherol in an amount ranging from about 47% to 72% by weight, preferably 52% to 65% by weight, and most preferably about 60% by weight; d-gamma tocopherol in an amount ranging from about 9% to about 21% by weight, preferably 10% to 17% by weight, and most preferably about 12% by weight, and mixed tocopherols including d-beta tocopherol and d-delta tocopherol in an amount ranging from about 1% to about 10% by weight, preferably 2% to 7% by weight, and most preferably about 4% by weight.

Selenium is a nonmetallic trace element recognized as a nutrient essential to human health. Selenium reduces prostate cancer by improving the general health and immunity of the prostate. Selenium is also a natural vascular stimulant and immunity booster. Selenium activates glutathione peroxidase, one of the most potent antioxidants, that prevents the free radicals from attacking LDL cholesterol and prevents its conversion into its more artery-damaging, oxidized form. Selenium also helps to "thin" the blood. Selenium and vitamin E are synergistic and boost T cells levels. Selenium is present in the composition in an amount ranging from about 0.009% to 0.05% by weight, preferably 0.01% to 0.03% by weight, and most preferably about 0.02% by weight. When the composition does not include an herb component, selenium is present in the composition in an amount ranging from about 0.05% to 0.5% by weight, preferably 0.09% to 0.3% by weight, and most preferably about 0.1% by weight.

Lycopene, a non-provitamin A carotenoid, is the most efficient singlet-oxygen quencher among the natural carotenoids. There is an inverse association between dietary intake of lycopene and prostate cancer risk, and studies have shown that lycopene supplementation exhibits positive effects in patients with localized prostate cancer. Possible mechanisms by which lycopene prevents cancer include inhibition of growth and induction of differentiation in prostate cancer cells and gene regulation. Lycopene is present in the composition in an amount ranging from about 0.26% to 1% by weight, preferably 0.35% to 0.75% by weight, and most preferably about 0.6% by weight. When the composition does not include an herb component, lycopene is present in the composition in an amount ranging from about 0.5% to 5% by weight, preferably 1% to 4% by weight, and most preferably about 2% by weight.

Zinc prevents prostate cancer and improves the prostatic immune system. It also exerts an anti-inflammatory effect on the prostate. Additionally, zinc has been shown to improve male potency and sex drive, prevent cancer, benefit diabetics and prevent hair loss. Zinc is present in the composition in an amount ranging from about 1% to 21% by weight, preferably 1.2% to 5% by weight, and most preferably about 1.8% by weight. When the composition does not include an herb component, zinc is present in the composition in an amount ranging from about 2% to 11% by weight, preferably 4% to 9% by weight, and most preferably about 7% by weight.

Vitamin $B_6$ is a water-soluble vitamin that exists in three major chemical forms: pyridoxine, pyridoxal, and pyridoxamine. Vitamin $B_6$ boosts immunity and prevents cancer. Vitamin $B_6$ also prevents blood clots that can block arteries. A deficiency of vitamin $B_6$ can increase serum levels of homocysteine and lead to hardened, narrowed arteries. Other symptoms of vitamin $B_6$ deficiency include anemia, dermatitis, glossitis, depression, confusion and convulsions. When used in the composition, vitamin $B_6$ is present in an amount ranging from about 1% to 22% by weight, preferably 2% to 16% by weight, and most preferably about 3% by weight. When the composition does not include an herb component, vitamin $B_6$ is present in an amount ranging from about 4% to 27% by weight, preferably 10% to 16% by weight, and most preferably about 12% by weight.

Vitamin $B_{12}$'s primary functions are in the formation of red blood cells and the maintenance of a healthy nervous system. Vitamin $B_{12}$ is necessary for the rapid synthesis of DNA during cell division. A deficiency of vitamin $B_{12}$ can increase serum levels of homocysteine and disrupt DNA production causing formation of megaloblasts and ultimately anemia. When used in the composition, vitamin $B_{12}$ is present in an amount ranging from about 0.03% to 0.1% by weight, preferably 0.04% to 0.07% by weight, and most preferably about 0.06% by weight. When the composition does not include an herb component, vitamin $B_{12}$ is present in an amount ranging from about 0.1% to 1% by weight, preferably 0.2% to 0.7% by weight, and most preferably about 0.3% by weight.

Folic acid, also known as folate and folacin, is a water-soluble B vitamin that occurs naturally in food. Folic acid is involved in the synthesis, repair and functioning of DNA, and a deficiency of folate may result in increased serum levels of homocysteine and damage to DNA that may lead to cancer. Folic acid can improve the endothelial function in patients with coronary artery disease. When used in the composition, folic acid is present in an amount ranging from about 0.1% to 2.5% by weight, preferably 0.15% to 1% by weight, and most preferably about 0.24% by weight. When the composition does not include an herb component, vitamin folic acid is present in an amount ranging from about 0.5% to 5% by weight, preferably 0.8% to 2% by weight, and most preferably about 1% by weight.

The methods for combining the herbs, vitamins and micronutrients of the present invention are well known to those of ordinary skill in the art and may be accomplished at a number of commercial production laboratories around the world including, for example The Chemins Company, Inc., located in Colorado Springs, Colo.

In a preferred embodiment of the invention, the active ingredients of the composition include approximately 124 mg of d-alpha tocopheryl succinate, approximately 25 mg of d-gamma tocopherol, approximately 9 mg of mixed tocopherols including d-delta tocopherol and d-beta tocopherol, approximately 200 mcg of selenium chelate, approximately 5 mg of lycopene complex, approximately 15 mg of zinc gluconate, approximately 2 mg of folic acid, approximately 500 mcg of cyanocobalamin and approximately 25 mg of pyridoxine HCL.

In another preferred embodiment of the invention, the active ingredients of the composition include approximately 60% by weight of d-alpha tocopheryl succinate, approximately 12% by weight of d-gamma tocopherol, approximately 4% by weight of mixed tocopherols including d-delta tocopherol and d-beta tocopherol, approximately 0.1% by weight of selenium chelate, approximately 2.4% by weight of lycopene complex, approximately 7.3% by weight of zinc gluconate, approximately 1% by weight of folic acid, approximately 0.24% by weight of cyanocobalamin and approximately 12% by weight of pyridoxine HCL.

In yet another preferred embodiment of the present invention, the active ingredients of the composition include approximately 52% to 65% by weight of d-alpha tocopheryl succinate, approximately 10% to 17% by weight of d-gamma tocopherol, approximately 2% to 7% by weight of mixed tocopherols including d-delta tocopherol and d-beta tocopherol, approximately 0.09% to 0.3% by weight of selenium chelate, approximately 1% to 4% by weight of lycopene complex, approximately 4% to 9% by weight of zinc gluconate, approximately 0.8% to 2% by weight of folic acid, approximately 0.2% to 0.7% by weight of cyanocobalamin and approximately 10% to 16% by weight of pyridoxine HCL.

In a preferred embodiment of the invention including an herb component, the active ingredients of the composition include approximately 320 mg of saw palmetto, approximately 62 mg of d-alpha tocopheryl succinate, approximately 12.5 mg of d-gamma tocopherol, approximately 4.5 mg of mixed tocopherols including d-delta tocopherol and d-beta tocopherol, approximately 100 mcg of selenium chelate, approximately 2.5 mg of lycopene complex, approximately 7.5 mg of zinc gluconate, approximately 1 mg of folic acid, approximately 250 mcg of cyanocobalamin and approximately 12.5 mg of pyridoxine HCL.

In another preferred embodiment of the invention including an herb component, the active ingredients of the composition include about 76% by weight of saw palmetto, about 15% by weight of d-alpha tocopheryl succinate, about 3% by weight of d-gamma tocopherol, about 1% by weight of mixed tocopherols including d-delta tocopherol and d-beta tocopherol, about 0.02% by weight of selenium chelate, about 0.6% by weight of lycopene complex, about 1.8% by weight of zinc gluconate, about 0.24% by weight of folic acid, about 0.06% by weight of cyanocobalamin and about 3% by weight of pyridoxine HCL.

In yet another preferred embodiment of the present invention including an herb component, the active ingredients of the composition include approximately 60% to 80% by weight of saw palmetto, approximately 12% to 20% by weight of d-alpha tocopheryl succinate, approximately 2% to 7% by weight of d-gamma tocopherol, approximately 0.75% to 3% by weight of mixed tocopherols including d-delta tocopherol and d-beta tocopherol, approximately 0.01% to 0.03% by weight of selenium chelate, approximately 0.35% to 0.75% by weight of lycopene complex, approximately 1.2% to 5% by weight of zinc gluconate, approximately 0.15% to 1% by weight of folic acid, approximately 0.04% to 0.07% by weight of cyanocobalamin and approximately 2% to 16% by weight of pyridoxine HCL.

Preferably, the compositions of the present invention are prepared in a caplet dosage form, however it will be understood by those skilled in the art that other dosage forms may also be suitably prepared by known methods, for example, capsules, tablets, powders, pastes, liquids and similar dosage forms. Solid dosage forms for oral administration include caplets, capsules, tablets, pills, powders, and granules. Solid dosage forms of the present invention may be created using any pharmaceutically acceptable excipients such as fillers or extenders, binders, humectants, disintegrating agents, wetting agents and lubricants. Suitable pharmaceutically acceptable excipients are described in "Remington: The Science and Practice of Pharmacy," Lippincott Williams & Wilkins, Baltimore, Md. (2000), incorporated herein by reference.

The solid dosage forms of tablets, capsules, powders and granules can be prepared with coatings and shells such as enteric coatings and other coatings well known in the pharmaceutical formulating art. They may optionally contain opacifying agents and can also be of a composition that they release the active ingredients only, or preferentially, in a certain part of the intestinal tract, optionally, in a delayed manner.

Liquid dosage forms for oral administration include pharmaceutically acceptable emulsions, solutions, suspensions, syrups and elixirs. In addition to the active ingredients, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

The compositions are preferably administered in spaced dosages throughout the day, for example, administered every three to twelve hours, so as to maintain the level of active ingredients in the system of the host. Preferably, the dose is administered every 12 hours.

The following examples will serve to further typify the nature of the invention but are not limiting on the scope thereof, which is defined solely by the appended claims.

EXAMPLE 1

Caplets, each containing the following active ingredients for treatment or prevention of BHP, prostate cancer and/or vascular disease:
320 mg saw palmetto extract, yielding 144 mg of fatty acids and sterols
62 mg of d-alpha tocopheryl succinate
12.5 mg of d-gamma tocopherol
4.5 mg of mixed tocopherols including d-delta tocopherol and d-beta tocopherol
100 mcg of selenium chelate
2.5 mg of lycopene complex
7.5 mg of zinc gluconate
1 mg of folic acid
250 mcg of cyanocobalamin
12.5 mg of pyridoxine HCL Other ingredients include dicalcium phosphate as a tableting excipient and carrier for folic acid and cyanocobalamin; cellulose as a tableting excipient; maltodextrin as a carrier for saw palmetto extract and natural vitamin E oils; microcrystalline cellulose as a tableting excipient; modified corn starch as a tableting excipient; soy protein, enzymes, sodium selenite and citric acid contained within the selenium chelate; silica as a tableting excipient; sucrose and corn starch contained in the lycopene complex; polyvinylpyrrolidone as a tableting excipient; magnesium stearate as a tableting excipient and titanium dioxide, polydextrose, hydroxypropyl methylcellulose, triacetin and polyethylene glycol as coating ingredients.

EXAMPLE 2

Caplets, each containing the following active ingredients for treatment or prevention of prostate cancer and/or vascular disease:
124 mg of d-alpha tocopheryl succinate
25 mg of d-gamma tocopherol
9 mg of mixed tocopherols including d-delta tocopherol and d-beta tocopherol
200 mcg of selenium chelate
5 mg of lycopene complex
15 mg of zinc gluconate
2 mg of folic acid
500 mcg of cyanocobalamin
25 mg of pyridoxine HCL.

Other ingredients include dicalcium phosphate as a tableting excipient and carrier for folic acid and cyanocobalamin; cellulose as a tableting excipient; maltodextrin as a carrier for natural vitamin E oils; microcrystalline cellulose as a tableting excipient; modified corn starch as a tableting excipient; soy protein, enzymes, sodium selenite and citric acid contained within the selenium chelate; silica as a tableting excipient; sucrose and corn starch contained in the lycopene complex; polyvinylpyrrolidone as a tableting excipient; magnesium stearate as a tableting excipient and titanium dioxide, polydextrose, hydroxypropyl methylcellulose, triacetin, ethyl cellulose, ammonium hydroxide, fractionated coconut oil, oleic acid and polyethylene glycol as coating ingredients.

What is claimed is:

1. A dietary supplement, the active components thereof consisting essentially of,
    a first component selected from the group consisting of *Echinacea*, saw palmetto, stinging nettle, pumpkin seed, *Pygeum africanum* and combinations thereof,
    a vitamin E component,
    a selenium component,
    a lycopene component,
    a zinc component, and
    a vitamin B component.

2. The dietary supplement according to claim 1 wherein the first component is saw palmetto.

3. The dietary supplement according to claim 1 wherein the vitamin E component comprises d-gamma tocopherol.

4. The dietary supplement according to claim 1 wherein the vitamin E component comprises d-alpha tocopherol.

5. The dietary supplement according to claim 1 wherein the vitamin E component comprises d-beta tocopherol and d-delta tocopherol.

6. The dietary supplement according to claim 1 wherein the vitamin B component comprises vitamin $B_{12}$.

7. The dietary supplement according to claim 1 wherein the vitamin B component comprises vitamin $B_6$.

8. The dietary supplement according to claim 1 wherein the vitamin B component comprises folic acid.

9. The dietary supplement according to claim 1 wherein the first component comprises from about 60% to about 80% by weight of the active components.

10. The dietary supplement according to claim 3 wherein d-gamma tocopherol comprises from about 2% to about 7% by weight of the active components.

11. The dietary supplement according to claim 4 wherein d-alpha tocopherol comprises from about 12% to about 20% by weight of the active components.

12. The dietary supplement according to claim 5 wherein d-beta tocopherol and d-delta tocopherol comprise from about 0.75% to about 3% by weight of the active components.

13. The dietary supplement according to claim 6 wherein vitamin $B_{12}$ comprises from about 0.04% to about 0.07% by weight of the active components.

14. The dietary supplement according to claim 7 wherein vitamin $B_6$ comprises from about 2% to about 16% by weight of active components.

15. The dietary supplement according to claim 1 wherein the zinc component comprises from about 1.2% to about 5% by weight of the active components.

16. The dietary supplement according to claim 1 wherein the selenium component comprises from about 0.01% to about 0.03% by weight of the active components.

17. The dietary supplement according to claim 1 wherein the lycopene component comprises from about 0.35% to about 0.75% by weight of the active components.

18. The dietary supplement according to claim 8 wherein folic acid comprises from about 0.15% to about 1% by weight of the active components.

19. The dietary supplement according to claim 1 wherein the first component includes from about 250 mg to about 340 mg of saw palmetto; the vitamin E component includes from about 50 mg to about 85 mg of d-alpha tocopherol, from about 8 mg to about 30 mg of d-gamma tocopherol and from about 3 mg to about 13 mg of a combination of d-delta tocopherol and d-beta tocopherol; the vitamin B component includes from about 0.6 mg to about 4.5 mg of folic acid, from about 0.15 mg to about 1.0 mg of vitamin $B_{12}$ and from about 5 mg to about 100 mg of vitamin $B_6$; the zinc component includes from about 5 mg to about 50 mg of zinc; the selenium component includes from about 50 mcg to about 200 mcg of selenium, and the lycopene component includes from about 1 mg to about 4 mg of lycopene.

20. The dietary supplement according to claim 1 wherein the first component includes approximately 320 mg of a saw palmetto; the vitamin E component includes approximately 62 mg of d-alpha tocopheryl succinate, approximately 12.5 mg of d-gamma tocopherol and approximately 4.5 mg mixed of tocopherols including d-delta tocopherol and d-beta tocopherol; the vitamin B component includes approximately 1 mg of folic acid, approximately 250 mcg of vitamin $B_{12}$ and approximately 12.5 mg of vitamin $B_6$; the zinc component includes approximately 7.5 mg of zinc gluconate; the selenium component includes approximately 100 mcg of selenium chelate, and the lycopene component includes approximately 2.5 mg of lycopene complex.

21. The dietary supplement according to claim 1 wherein the active components consist essentially of about 76% by weight of the first component, about 19% by weight of to vitamin E component, less than about 1% by weight of the selenium component less than about 1% by weight of the lycopene component, less than about 2% by weight of the zinc component and less than about 4% by weight of the vitamin B component.

22. A dietary supplement the active components thereof consisting of,
d-alpha tocopherol,
d-gamma tocopherol,
additional tocopherol selected from a group consisting of d-beta tocopherol, d-delta tocopherol and a mixture of d-beta tocopherol and d-delta tocopherol,
selenium,
lycopene,
zinc,
folic acid,
vitamin $B_{12}$, and
vitamin $B_6$.

23. A dietary supplement, the active components thereof consisting of,
d-alpha tocopherol,
d-gamma tocopherol,
additional tocopherol selected from a group consisting of d-beta tocopherol, d-delta tocopherol and a mixture of d-beta tocopherol and d-delta tocopherol,
selenium,
lycopene,
zinc,
folic acid,
vitamin $B_{12}$.
vitamin $B_6$ and
a first component selected from a group consisting of saw palmetto, *Echinacea*, stinging nettle, pumpkin seed, *Pygeum africanum* and combinations thereof.

24. The dietary supplement according to claim 23 wherein the active components consist of from about 250 mg to about 340 mg of saw palmetto, from about 50 mg to about 85 mg of d-alpha tocopherol, from about 8 mg to about 30 mg of d-gamma tocopherol, from about 3 mg to about 13 mg of the additional tocopherol, from about 0.6 mg to about 4.5 mg of folic acid, from about 0.15 mg to about 1.0 mg of vitamin $B_{12}$, from about 5 mg to about 100 mg of vitamin $B_6$, from about 5 mg to about 50 mg of zinc, from about 50 mcg to about 200 mcg of selenium, and from about 1 mg to about 4 mg of lycopene.

25. The dietary supplement according to claim 23 wherein the active components consist of approximately 320 mg of saw palmetto, approximately 62 mg of d-alpha tocopherol as d-alpha tocopherly succinate, approximately 12.5 mg of d-gamma tocopherol, approximately 4.5 mg of the additional tocopherol, approximately 100 mcg of selenium as selenium chelate, approximately 2.5 mg of lycopene, approximately 7.5 mg of zinc as zinc gluconate, approximately 1 mg of folic acid, approximately 250 mcg of vitamin $B_{12}$ and approximately 12.5 mg of vitamin $B_6$.

26. The dietary supplement according to claim 23 wherein the active components consist of about 76% by weight of saw palmetto, about 15% by weight of d-alpha tocopherol, about 3% by weight of d-gamma tocopherol, about 1% by weight of the additional tocopherol, about 0.02% by weight of selenium, about 0.6% by weight of lycopene, about 1.8% by weight of zinc, about 0.24% by weight of folic acid, about 0.06% by weight of vitamin $B_{12}$ and about 3% by weight of vitamin $B_6$.

27. The dietary supplement according to claim 22 wherein the active components consist of approximately 124 mg of d-alpha tocopherol, approximately 25 mg of d-gamma tocopherol, approximately 9 mg of the additional tocopherol, approximately 200 mcg of selenium, approximately 5 mg of lycopene, approximately 15 mg of zinc, approximately 2 mg of folic acid, approximately 500 mcg of vitamin $B_{12}$ and approximately 25 mg of vitamin $B_6$.

28. The dietary supplement according to claim 22 wherein active components consist of about 60% by weight of d-alpha tocopherol, about 12% by weight of d-gamma tocopherol, about 4% by weight of the additional tocopherol, about 0.1% by weight of selenium, about 2.4% by weight of lycopene, about 7.3% by weight of zinc, about 1% by weight of folic acid, about 0.24% by weight of vitamin $B_{12}$ and about 12% by weight of vitamin $B_6$.

29. The dietary supplement according to claim 22 wherein the active components consist of approximately 52% to 65% by weight of d-alpha tocopherol, approximately 10% to 17% by weight of d-gamma tocopherol, approximately 2% to 7% by weight of the additional tocopherol, approximately 0.09% to 0.3% by weight of selenium, approximately 1% to 4% by weight of lycopene, approximately 4% to 9% by weight of zinc, approximately 0.8% to 2% by weight of folic acid, approximately 0.2% to 0.7% by weight of vitamin $B_{12}$ and approximately 10% to 16% by weight of vitamin $B_6$.

30. The dietary supplement according to claim 23 wherein the active components consist of approximately 320 mg of saw palmetto, approximately 62 mg of d-alpha tocopherol, approximately 12.5 mg of d-gamma tocopherol, approximately 4.5 mg of the additional tocopherol, approximately 100 mcg of selenium, approximately 2.5 mg of lycopene, approximately 7.5 mg of zinc, approximately 1 mg of folic acid, approximately 250 mcg of vitamin $B_{12}$ and approximately 12.5 mg of vitamin $B_6$.

* * * * *